(12) United States Patent
Fodor et al.

(10) Patent No.: US 6,703,529 B1
(45) Date of Patent: Mar. 9, 2004

(54) PROCESS FOR OXIDATION OF CYCLOHEXANE

(75) Inventors: Ludovic Fodor, Beaumont, TX (US); Bhagya Chandra Sutradhar, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/242,544

(22) Filed: Sep. 12, 2002

(51) Int. Cl.[7] .................. C07C 45/27; C07C 29/20; C07C 35/08
(52) U.S. Cl. .................. 568/342; 568/344; 568/835; 568/836
(58) Field of Search .................. 568/342, 344, 568/835, 836

(56) References Cited

U.S. PATENT DOCUMENTS

| 4,465,861 A | 8/1984 | Hermolin |
| 4,720,592 A | 1/1988 | Besmar et al. |
| 5,932,109 A | 8/1999 | Griffin |
| 6,008,415 A | * 12/1999 | Greene et al. .............. 568/358 |

FOREIGN PATENT DOCUMENTS

| JP | 2001 58192 | 3/2001 |
| RU | 1323537 | 7/1987 |
| RU | 2023674 | 11/1994 |

* cited by examiner

*Primary Examiner*—Shailendra Kumar
*Assistant Examiner*—Sikarl A. Witherspoon

(57) ABSTRACT

Disclosed herein is a process for the production of a mixture of cyclohexanone and cyclohexanol by oxidation of cyclohexane and decomposition of cyclohexyl hydroperoxide.

9 Claims, 1 Drawing Sheet

PROCESS FOR OXIDATION OF CYCLOHEXANE

FIELD OF THE INVENTION

The present invention relates to a process for the production of cyclohexanol, cyclohexanone and cyclohexyl hydroperoxide from a cyclohexane oxidation process.

BACKGROUND OF THE INVENTION

Oxidation of cyclohexane by air produces a reaction product comprising cyclohexanol (A), cyclohexanone (K) cyclohexyl-hydroperoxide (CHHP) and small amounts of by-products. The reaction product is treated with water followed by separation of organic and aqueous phases. The organic phase comprising A, K and CHHP is further treated to cause decomposition of CHHP to K and A. Therefore, K and A are the main product of the overall process, their mixture is commonly known as "KA-oil".

Several byproducts formed during the above processes remain as impurities mixed with KA oil (crude) along with unreacted cyclohexane. Refined KA oil is produced from crude KA oil by distillation. All the byproducts, catalysts, additives, corrosion derived metal compounds form what is referred to as the "tails" of the distillation column (U.S. Pat. No. 4,720,592). In order to eliminate the by-products produced during the process, the KA oil is distilled in the final step. The material that remains after the KA distillation is a viscous material, usually dark in color, comprising the impurities formed during the process, the non-volatile catalysts, and any additives that were used in the process. Collectively these materials are referred to as "Non Volatile Residue" or "NVR"). The tails stream is often concentrated through evaporation. The concentrated stream, commonly known as non-volatile residue (NVR) is often disposed of as boiler fuel.

Corrosion in process vessels made of stainless steel adds chromium to NVR. In addition, for a CHHP decomposition process using chromium catalyst (U.S. Pat. No. 4,465,861), the chromium ends up in the NVR. Typically, a concentration of chromium in the range of 2–100 ppm is observed in NVR. Upon combustion in a boiler, the chromium forms a part of the emission through boiler stack gas. In order to comply with environmental regulations, the stack gas needs expensive treatment for chromium reduction. Alternative routes to disposal of NVR are also expensive.

It is, therefore, desirable to have process of oxidation of cyclohexane to produce KA oil, the said process comprising one or more steps to reduce chromium content of NVR so the stack gas corresponding to its combustion will contain an acceptable low concentration of chromium.

The NVR is an aqueous dispersion. Typically, the composition comprises formic acid, acetic acid, butyric acid, valeric acid, caproic acid, 6-hydroxycaproic acid, succinic acid, glutaric acid, adipic acid, phosphoric acid organic esters, chromium salts, and other materials.

The amount of NVR formed during KA production is significant, it may represent up to 20% of the amount of KA oil produced and normally it is disposed by burning and getting credit for the fuel value. Because of more demanding environmental regulations the disposal of NVR with high chromium content by burning in boilers will be unacceptable.

There are known procedures to eliminate hexavalent chromium from heavy metal sludge or waste liquid, involving reducing the hexavalent chromium in acidic solution to trivalent (JP 2001058192 A 20010306). This procedure is not applicable for Cr elimination from NVR because all the NVR will be solubilized during treatment in water.

There are also treatment systems available to eliminate chromium from plating operations (U.S. Pat. No. 5,932,109) by precipitating using hydrazine or Al and Cu shavings (RU 2,023,674) by adding calcium hydroxide to specified pH value then barium hydroxide to further increase pH (SU 1323537).

The object of the present invention is to provide a method for producing KA oil and having NVR by-product with low Cr concentration.

Figure 1:
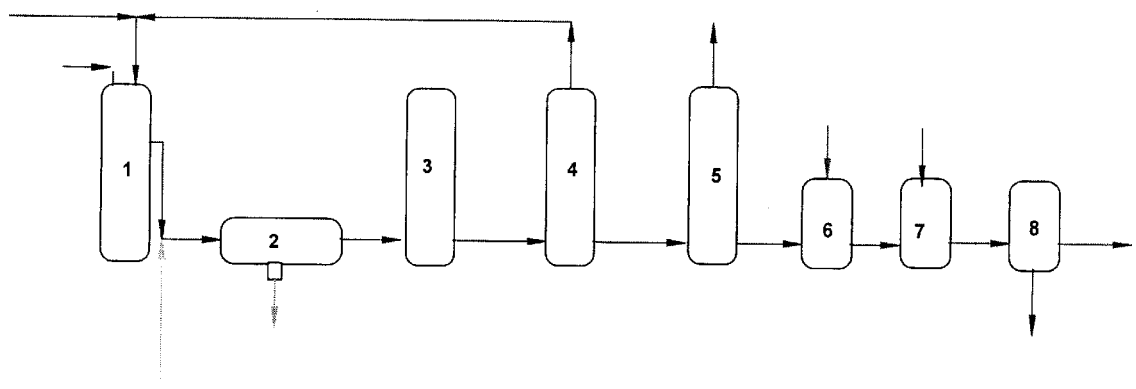
FIG. 1 is a schematic flow chart of the process of the present invention, and is provided to aid in the understanding of the process. The Air oxidizer (1) is used to oxidize the cyclohexane. The water separator (2) is used to collect the aqueous phase that results from step 1 of the present process. Cyclohexyl hydroperoxide that is present in a second phase is decomposed in a CHHP decomposition reactor (3) to cyclohexanone and cyclohexanol. These products are distilled in a distillation column (4) and then KA refined in a refiner (5). The NVR that remains in the refiner (5) is then contacted with first, either a dilute acid (6) or with an aqueous electrolyte solution (7) to extract chromium. Finally, a phase separator (8) is used to separate the chromium into the aqueous phase.

Cyclohexane is air oxidized in a tower oxidizer (1) and the oxidizer tails are contacted with water. The water is separated in a decanter (2) into a first phase and second phase. The first phase comprising substantially aqueous (water-soluble) components and said second phase comprising cyclohexanol and organic components. The water washed organic phase is directed to the CHHP decomposition reactor (3) where it is treated with chromium octoate and is decomposed in K and A. The cyclohexane is recovered by distillation (4) and recycled. The resulting crude KA oil is refined in the KA refiner (5) and the KA is distilled of at the top of the column. The NVR is collected at the bottom of refining column. The resulted NVR is contacted with an acidic solution in the acid treatment reactor (6). The non-volatile residue is further contacted with an electrolyte solution (7), followed by separation of the aqueous phase from the organic phase (8). The separated organic phase is the NVR with low Cr concentration (~2 ppm).

SUMMARY OF THE INVENTION

Disclosed herein is a process for the production of cyclohexanone and cyclohexanol mixture from cyclohexane together with by product recovery, said process comprising: (i) oxidizing cyclohexane to obtain air oxidation tails; (ii) contacting the air oxidation tails with water; (iii) separating the mixture resulting from step (ii) into a first phase and a second phase, said first phase comprising substantially aqueous components and said second phase comprising cyclohexyl hydroperoxide and organic components; (iv) decomposing the cyclohexyl hydroperoxide in the organic phase from step (iii) to cyclohexanone and cyclohexanol; (v) refining of the cyclohexanol and cyclohexanone mixture obtained in step (iv) and (vi) separating chromium from nonvolatile residue.

DETAILED DESCRIPTION OF THE INVENTION

Disclosed herein is a method for oxidizing cyclohexane, which subsequently will produce NVR by-product with low Cr content. In the method of the present invention the cyclohexane is contacted with air in the air oxidizer (1) at temperatures between about 100° C. to about 175° C. The air oxidizer can be an oxidation tower, stirred or non-stirred tank reactor(s), stirred or non-stirred autoclave(s). The air oxidizer tails are contacted with water. The ratio between the air oxidizer tails and water is about 100:1. After the aqueous phase is separated (2) the cyclohexyl-hydroperoxide is decomposed to K and A (3).

Decomposition of the CHHP may be accomplished using thermal decomposition, catalytic decomposition, catalytic hydrogenation or other catalytic methods such as the use of gold catalyst, for example. Thermal decomposition is carried out at relatively high temperatures, 120–175° C. and long hold-up times.

CHHP hydrogenation is carried out with heterogeneous catalysts, at temperatures between about 100 to about 160° C. Hydrogenation catalysts include but not limited to palladium on silica or alumina support.

CHHP decomposition may also be accomplished without hydrogen with the use of different heterogeneous catalysts such as gold deposited on silica or alumina at temperatures between 100–160° C.

CHHP decomposition may also be accomplished by metal catalyzed decomposition in caustic aqueous solution. This is done by contacting the CHHP with cobalt, chromium, or a mixture thereof, in caustic solutions, preferably sodium hydroxide. When using either or both of these metals for CHHP decomposition the concentration of Co and/or Cr is between 0.1 and 20 ppm.

After the CHHP is transformed to K&A the excess cyclohexane is distilled off (4) and the resulting KA oil is distilled in KA Refiner at temperatures between from about 90 to about 170° C. (5). Some of the process steps, such as water washing the AOR tails, are beneficial in reducing deactivation of the catalyst but are not essential. Also the cyclohexane distillation and KA oil refining can be performed by different unit operations such as vacuum distillation, steam distillation, etc.

The NVR remaining in the bottom of the KA Refiner column (5) is sent to acid treatment reactor (6). The NVR is contacted in (6) with diluted acid solutions (0.2–10%) at temperatures between about 60 to about 120° C. After the first hydrolysis stage the NVR is contacted with an aqueous electrolyte solution (7) to extract the Cr into the aqueous layer. The extraction step of the Cr in aqueous electrolyte solution can be accomplished at temperatures between about 20 to about °120° C. The NVR with reduced Cr is separated from the aqueous electrolyte solution in a decanter (8). Depending on actual process parameters, the extraction and hydrolysis steps may need to be repeated in order to reduce the Cr to very low levels. The hydrolysis and extraction steps can be reversed in order.

The K and A is obtained as a mixture. The product (K and A) is oxidized to produce adipic acid. The oxidizing agent that may be used is nitric acid. The resulting adipic acid may be used in turn to make Nylon products, pharmaceutical additives, food additives, polyurethane, and a host of other applications.

What is claimed is:

1. A process for the production of cyclohexanone and cyclohexanol mixture from cyclohexane together with byproduct recovery, said process comprising:

(i) oxidizing cyclohexane to obtain air oxidation tails;

(ii) contacting the air oxidation tails with water;

(iii) separating the mixture resulting from step (ii) into a first phase and a second phase, said first phase comprising substantially aqueous components and said second phase comprising cyclohexyl hydroperoxide and organic components;

(iv) decomposing the cyclohexyl hydroperoxide in the organic phase from step (iii) to cyclohexanone and cyclohexanol;

(v) refining of the cyclohexanol and cyclohexanone mixture obtained in step (iv) and (vi) separating chromium from nonvolatile residue produced in step (v) by either (step a) contacting the non-volatile residue or at least a portion of the organic content of the non-volatile residue with an acidic compound, or (step b) contacting the non-volatile residue or at least a portion of the organic content of the non-volatile residue with an aqueous electrolyte solution, followed by separation of the aqueous phase from the organic phase, or both (step a) and (step b) sequentially, or (step b) and (step a) sequentially.

2. A process according to claim 1 wherein the decomposition of CHHP is accomplished by thermal decomposition, by catalytic decomposition, or catalytic hydrogenation.

3. A process according to claim 2 wherein the decomposition of CHHP is accomplished by metal catalyzed decomposition in caustic solution.

4. A process according to claim 2 wherein the catalyst comprises Co, Cr, or both.

5. A process according to claim 3 wherein the catalyst comprises Au and Pd.

6. A process according to claim 2 wherein the decomposition of CHHP is carried out at a temperature between about 100° C. to about 175° C.

7. A process according to claim 1 refining of the cyclohexanol and cyclohexanone mixture is accomplished by distillation.

8. A process according to claim 1 wherein the air oxidation tails is washed with water.

9. A process according to claim 1 wherein the cyclohexanol and cyclohexanone product obtained are used to produce adipic acid.

* * * * *